United States Patent [19]
Matthews, Larry S. et al.

[11] Patent Number: 4,741,345
[45] Date of Patent: May 3, 1988

[54] CONTINUOUS FLOW TISSUE PRESSURE MEASUREMENT

[75] Inventors: Matthews, Larry S.; Steven A. Goldstein, both of Ann Arbor, Mich.

[73] Assignee: Board of regents of the University of Michigan, Ann Arbor, Mich.

[21] Appl. No.: 892,264

[22] Filed: Aug. 4, 1986

Related U.S. Application Data

[62] Division of Ser. No. 699,049, Feb. 7, 1985.

[51] Int. Cl.$^4$ .............................................. A61B 5/02
[52] U.S. Cl. .................................... 128/675; 128/748; 604/280
[58] Field of Search ............... 128/632, 637, 673, 675, 128/748; 604/96–100, 103, 280, 281; 73/747–750

[56] References Cited

U.S. PATENT DOCUMENTS 2,103,371  4/1934  Kleckner .......................... 128/400
3,483,859  12/1969  Pittman ................................ 604/96
4,205,691  6/1980  Patel ..................................... 604/280
4,214,593  7/1980  Imbruce et al. ...................... 604/96

Primary Examiner—Kyle L. Howell
Assistant Examiner—Randy Citrin
Attorney, Agent, or Firm—Robert B. Stevenson

[57] ABSTRACT

This invention provides a means of measuring tissue pressure in muscle compartments and other regions in humans and other animals. An appropriate length, for example, 6 to 12 inches of thin plastic tubing, typically less than 3 mm outside diameters, is prepared as a working part of the tissue pressure transducer. A portion of the plastic tubing including the thin wall section such as a bubble is inserted into the muscle tissue for which pressure measurement is desired to be made. A fluid is circulated through the tubing at a constant flow rate. When the internal pressure of the tubing is greater than the external pressure, the bubble expands and there is no increase in the flow resistance of the system. When the pressure on the outside exceeds the normal system operating pressure, the thin wall section or bubble contacts, resistance to flow increases, and the system pressure increases. This increase in system pressure is directly proportional to tissue pressure.

2 Claims, 3 Drawing Sheets

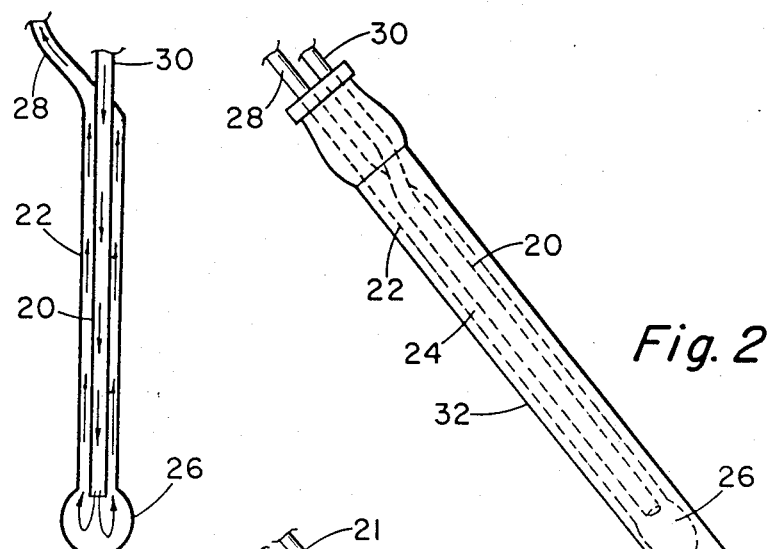
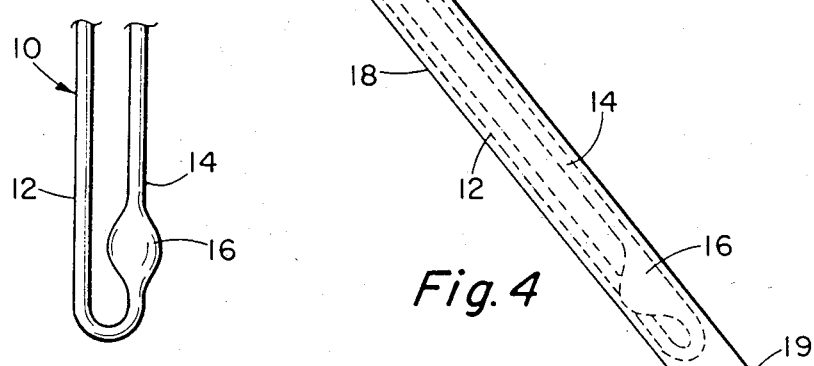
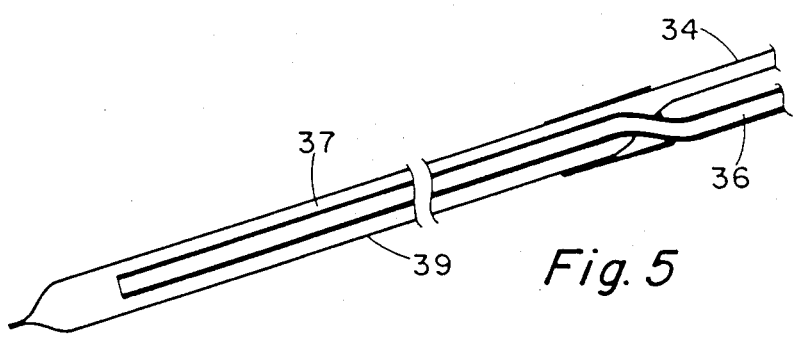

| CATHETER DIMENSIONS (IN MILLIMETERS) | | | |
|---|---|---|---|
| A | B | C | D |
| 6.17 | 4.32 | 13.41 | 1.75 |

CONTINUOUS FLOW TISSUE PRESSURE MEASUREMENT

This is a division of co-pending application Ser. No. 699,049 filed on Feb. 7, 1985.

BACKGROUND OF THE INVENTION

1. Field of the Invention.

This invention relates to a system of measuring tissue pressure in muscle compartments and other regions in humans and other animals. The system of this invention provides for obtaining absolute measurement values and changes in measured values with time and is useful in the diagnosis of muscle tissue compartment syndromes, tissue responses to vascular ischemia, and any disease or condition which involves increases in tissue or fluid pressure.

Specifically, this invention will be useful in the diagnosis and management of muscle compartment syndromes. For an article on acute compartment syndromes, reference is made to J. Bone Joint Surg., 60A: 1091-1095, 1978. In general, these conditions arise as a result of the trauma; frequently from fractures of the lower extremity. After such an injury, the anterior compartment and/or other compartments of the leg may swell. The increased intercompartmental pressure caused by the tissue edema and accumulation of interstitial fluid raises the compartmental pressure above venous levels which occludes venous outflow or drainage from the compartment. With this occlusion, intercompartmental pressure rises further. When the compartmental pressure rises above normal, (pressure of approximately 0 to 30mm Hg) functional capillary flow through the capillary beds stops. At this point, oxygen and fresh nutrients are not provided to the muscles, neural and other tissues in the compartment. Widespread tissue ischemia begins and with time, tissue necrosis occurs. This point is generally reached at a compartment pressure of approximately 35 to 45 mm of mercury. With early tissue necrosis, the pressure continues to rise. The end result can be a great loss of muscle and other tissues within the involved compartment and the loss of associated function for the individual.

2. Prior Art.

The traditional method of compartment syndrome diagnosis includes an observation of blood availability to the most distal parts of the extremity, the fingers and toes. The return of a pink color after pressure application to the distal parts was believed to indicate a satisfactory blood supply. The presence of pulses in the distal small arteries was thought to be a favorable factor. Pain, particularly on passive motion of the finger or toes; the observation of gross limb swelling; and "woody" feeling of the involved limb are classic positive diagnostic criteria.

In 1975, Whitesides, Haney and Morimoto described the use of a syringe, monometer intravenous tubing, and open hypodermic needle to measure suspect compartment pressure. It was published in Clin. Orthop., 113; 43-51. Another system developed for determining the pressure within a tissue which is called the "wick catheter" and was reported by Mubarak, et al J. Bone Joint Surg., 58A; 1016-1020, 1976. Mubarak, et al used a simple manometric system and used a catheter containing a fibrous material which protruds slightly outside the catheter itself. This was meant to push away muscle tissue and prevent occlusion of the catheter with changes in pressure. Because of the continued difficulty with occlusion and clogging of the devices used in the Whiteside system and in the Mubarak system, a "slit catheter" compartment pressure measuring device was developed by Rorabeck, et al Canad. J. Surg., 15: 249, 1972.

The devices and techniques just described in general have improved the clinicians ability to diagnose compartment criteria. However, they are not without shortcomings. For example, the method of observation of capillary refill of distal pulses and other observations of distal blood flow, fail to account for the fact that there are usually several arterial supplies to the distal limb. There can be complete necrosis of a given compartment in the face of continuous presence of pulsatile distal blood flow. In addition, a major artery passing through an involved compartment contains blood at pressures generally over 100 mm of mercury. Whereas, on the other hand, a compartment pressure in excess of the danger zone, approximately 40 mm of mercury, could cause complete tissue necrosis and never impede pulsatile blood flow through the major artery. Pain and swelling occur with many injuries to the extremeties and are very subjective. The subjective nature of pain, swelling and a feeling of "woodiness" do not help in the discrimination of a compartment syndrome or tissue ischemia with swelling as compared to a contused or otherwise traumatized limb.

The hypodermic needle manometer technique for measurement of intracompartmental pressures, has several significant disadvantages. The muscle and other tissues within a compartment are not comparable to liquids. They more closely approximate a gel. Standard hydrostatic techniques cannot suffice in the measurement of such tissue pressures. With any reversed flow, there is occlusion of the tip of the needle by muscle or other tissue. Great excesses of pressure are required to free the catheters. No accurate pressure determination can be obtained under these circumstances. Repeated measurements by the same or different observers may, at times, provide substantially different measurement values within the range of clinical interest. Further, this type of device cannot be used effectively for continuous monitoring of compartment pressures since sterile saline or other liquid fluids must repeatedly be injected into the tissue. An injection of liquid into a closed compartment, in principal, raises the pressure in that compartment and could cause an increase in severity and extent of tissue necrosis and limb injury.

While the protruding wick, the slits, mentioned above help somewhat in preventing occlusion of the catheters by muscle and other tissues, these designs have not satisfactorily eliminated this problem. They all share the problem of introduction of additional liquid into an already swollen muscle compartment and with repeated usage, increase the danger of aggravating the condition. The reproducibility and accuracy of measurements made with these systems continue to be somewhat limited.

SUMMARY OF THE INVENTION

This invention concerns a system for determining pressure in animal tissue and comprises a tubing segment having at least one section of very thin construction. The tubing segment may be approximately 6 to 12 inches long and typically less than 3 mm outside diameter. The thin-walled section, or weak section, of the tubing segment may take on several forms. For example, it may be a bubble or bladder or there might just be a flattened region. The tubing segment is bent in a U-shape such that the two ends of the tubing lie parallel to each other. This bent portion containing the weak section may be called the measurement catheter. Means are provided such as a pump to flow fluid through the measurement catheter.

The measurement catheter is inserted, such as by use of a needle into the tissue for which the pressure is to be measured. After insertion into the tissue, the needle is withdrawn and the measurement catheter remains. One end of the tubing is connected to a pump means which provides, in the preferred embodiment, a constant flow of fluid through the measurement catheter. The other end of the tubing is connected to a tubing connected to a reservoir for supplying fluid to the pump. If the pressure in the tissue outside the measurement catheter is less than the pressure of the fluid flowing through the catheter, the bubble or (weak section) stays expanded and the pressure of the flowing fluid remains constant. However, if the pressure outside the thin-walled section is even slightly greater than the pressure inside the bubble, the thin-walled or weak section will deform inwardly. The collapsed or deformed thin section acts as a partial obstruction and causes increased resistance to the flow of fluid through the measurement catheter. For the fluid flow to remain constant, as dictated by the pumping system, the pressure on the inside of the system must rise. This rising pressure is made and recorded. This increase in system pressure is proportional to tissue pressure. Therefore, the instrument can be calibrated to directly read out the tissue pressure in millimeters of mecury.

As can be seen, it is an object of this invention to provide an improved means for determining the pressure in animal tissue such as swollen muscle compartments. This and other objects will become apparent and a better understanding of the invention shall be had from the following description taken in conjunction with the drawings.

BRIEF DESCRIPTION OF THE DRAWING

FIG. 1 illustrates a catheter consisting of coaxial thin-walled tubing.

FIG. 2 illustrates the catheter of FIG. 1 within an injection needle.

FIG. 3 illustrates a catheter having a bubble section.

FIG. 4 illustrates the catheter of FIG. 3 inside an injection needle.

FIG. 5 illustrates a thin-walled coaxial catheter.

DETAILED DESCRIPTION OF THE PREFERRED EMBODIMENT

Figure 6:
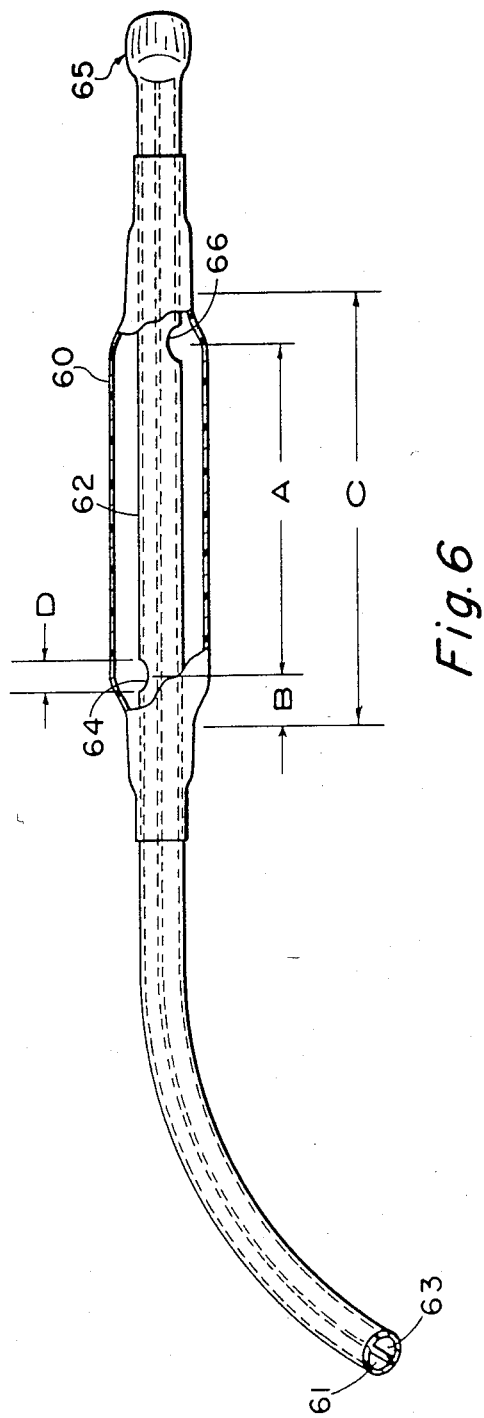
FIG. 6 illustrates still another and the preferred embodiment of a thin-walled catheter.

We will discuss various embodiments of measurement catheters of this invention. In general, it can be said that each such catheter would normally be a section of thin tubing, less than 3 mm in outside diameter, prepared as the working part of the tissue pressure transducer system. Each such catheter has a thin wall expansion section. This can be accomplished by having the wall of the expansion section thinner than the balance of the catheter. If the pressure outside the thin-walled expansion section is even slightly greater than the pressure inside the expansion section, the expansion section will collapse or deform inwardly. The thin-walled plastic expansion chamber or bubble allows measurement of differential pressures in tissues and gels.

Attention is now directed to the embodiments shown in FIG. 3. Shown thereon, is a catheter 10 having a U-shaped tube having parallel legs 12 and 14 with a bubble or bladder 16. The catheter is made of a plastic tubing having less than 3 mm outside diameter. The length of the catheter which is injected into the tissue is normally from 3 to 6 inches. The bubble 16 is made of thinner walls than the balance of the catheter legs 12 and 14. For example, the thickness of the legs 12 and 14 may be 0.8 mm and the thickness of the wall of the bubble may be 0.125 mm. The tubing may be made of any flexible material. The thin wall of the expansion section is such that it will deform inwardly if the pressure outside the wall is even only slightly greater than the pressure inside the bubble. A thin wall stainless steel needle may be used to introduct the measurement catheter of FIG. 3 into the tissue. In this regard, attention is directed to FIG. 4 which shows the measurement catheter of FIG. 3 inserted in the needle 18. In preparing the device of FIG. 4 for use, the deflated measurement bubble and complete catheter of FIG. 3 is easily deformed or folded to fit within the needle. The bladder section 16 is just above the tip 19 of the needle. After the needle is inserted into the muscle tissue for which pressure measurement is desired to be made, the needle 18 is withdrawn. To accomplish this, the catheter or end sections 20 and 23 of the catheter will be grasped by the operator and the needle 18 will be pulled up over the sections 21 and 23. The catheter 10 which is inside the needle 18 and includes the sections 12, 14 and bubble 16, will be allowed to unfold and expand within the tissue. After the needle 18 is withdrawn, the sections of 10 and 14 will be taped to the patient's skin.

Figure 7:
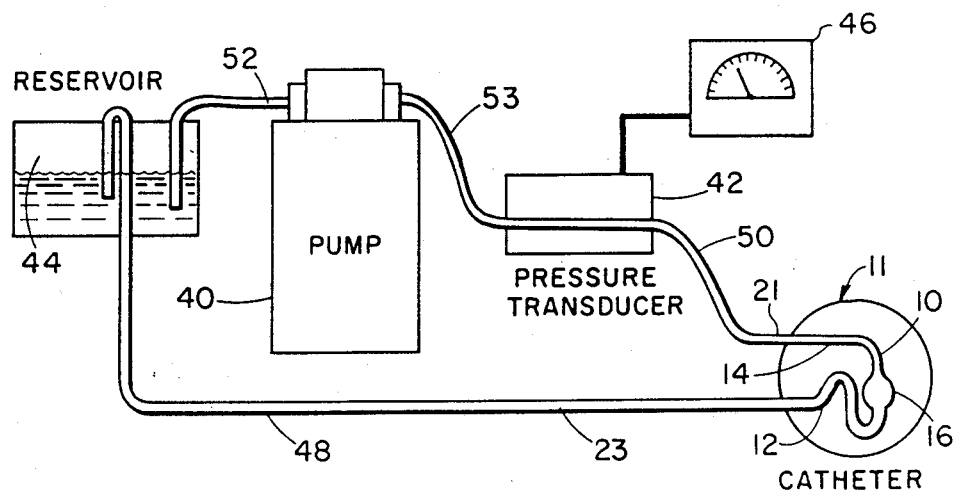
FIG. 7 illustrates the over-all measurement system.

Attention is next directed to FIG. 7 which shows a complete COMPALERT tissue pressure measurement transducer system. Shown thereon is the catheter 10 of FIG. 3 which has been inserted in muscle tissue symbolically indicated by reference number 11. The ends 21 and 23 are connected to tubings 50 and 48 respectively. Shown in FIG. 7 is a constant flow pump 40 having an input 52 which is connected to reservoir 44 and an output 53 which is connected to a pressure transducer 42 whose output is connected to conduit 50 which is directly connected to the measurement catheter 10. The outlet from catheter 10 is connected through tubing 48 to the reservoir 44. The pressure transducer is connected to a readout device 46. In a preferred embodiment, pump 40 is selected to deliver fluid under a constant flow rate over a wide range of operating circumstances. If the pressure in line 53 increases, the output flow rate from pump 40 nevertheless remains constant over the pressure range of interest. The pressure transducer 42 measures or monitors the pressure in tubing 53. If the pressure in the tissue represented by reference number 11 is low or normal, the bubble 16 will not deform inwardly and the pressure in the hose or tubing 53 remains constant and there is not appreciable resistence to flow across this region of the system having the measurement catheter. Thus, the pressure transducer 42 will record no significant pressure increase or change from that which is normal. However, if the pressure in tissue 11 increases and exceeds the normal system operating pressure, the bubble 16 will deform inwardly and act as a partial obstruction and cause an increased resistance to the flow of fluid through the system. For the fluid flow to remain constant as maintained by the pumping system, the pressure on the input side of the fluid flow path before the bubble 16 must rise. This rise in pressure is measured by pressure transducer 42 and recorded or otherwise displayed on instrumentation 46. The instrument can be calibrated to directly read out tissue pressure in mm of mercury. The preferred fluid which is used in this system and maintained in reservoir 44 is a saline solution and is pre-sterilized and maintained sterilized throughout the use of the invention for safety purposes. Further, all portions of the system which contact the patients, such as the catheter, can be disposed of after one use.

Figure 8:
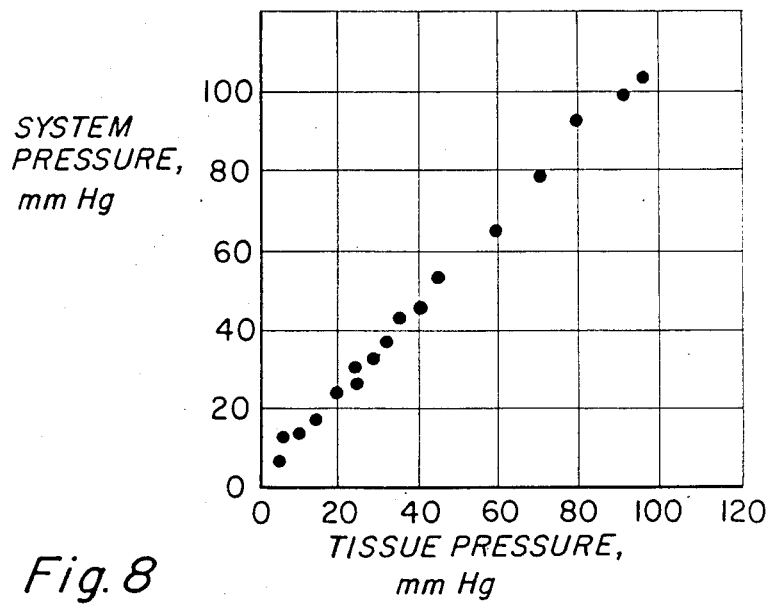
FIG. 8 illustrates a chart calibrating system pressure and tissue pressure.

Attention is next directed to FIG. 8 which shows an actual calibration curve of a working system using the embodiment depicted in FIG. 6. The pressure readout device 46 can be calibrated to directly read out tissue pressure in mm of mercury. The data shown in FIG. 8 was obtained using the catheter 10 of FIG. 7 submerged in an agar gel solution. Further, two biological methodology studies were performed. One utilized an intact canine cadaver extremity and the other isolated canine quadricep muscles. Calibration tests for the particular catheter design used will permit accurate readout of the fluid pressure within the tissue.

Referring back to FIG. 7, any suitable constant flow pump unit would prove satisfactory. The final selection will undoubtedly depend on cost, size and convenience of use. However, a suitable pump which appears to be universally available and would be appropriate is the Masterflex Pump, drive #K7543-01, 02, 06, 12, 20, 30 or 60, or drive #K7531-10. A suitable pressure measurement transducer which was used in studies made in this invention, was a SETRA model #205-2 pressure transducer with a range from 0 to 25 pounds per square inches available from Setra, Inc., 45 Nagog Park, Acton, Mass. 01720. This transducer was powered by a model #CM24.1 power supply marketed by the AAK Corporation, 747 River Street, Haverhill, Mass. 01830.

Attention will now be directed to other forms of measurement catheters. For example, attention is now directed to FIG. 1 which shows a coaxial catheter having an inner tube 20 and an outer tube 22 which are coaxil. The lower end of outer tubing 22 is provided with a thin-walled bubble 26. This thin-walled bubble 26 functions in a manner similar to the bubble 16 of the catheter of FIG. 3. Fluid flows through tubing end 30 down tubing 20 to the bubble 26 and up to end 28 of the outlet tubing. Tubing ends 30 and 28 would be directly connected into the conduits 50 and 48 respectively of the measurement device of FIG. 7. The theory of operation is the same of that for the catheter of FIG. 3. The coaxial catheter of FIG. 1 is shown in FIG. 2 as being contained in insertion needle 32. Again, the insertion will be similar to that described in relation to the device of FIG. 4. FIG. 5 illustrates still another form of the catheter. Here is provided a coaxial set of tubings including an inner tubing 37 and an outer thinwalled flexible tubing 39 which are connected to tubing ends 34 and 36. At least a portion of the tubing 39 is of a significantly thinner wall than that of inner tubing section 37. Flow is downwardly through inner tubing 37, and the end thereof, and out tubing 34. The portion of tubing 39 which is thin-walled, functions as the bladder or bubble 16 of FIG. 3. The catheter of FIG. 5 would be inserted into a needle such as 18 of FIG. 4 and would be inserted into the muscle tissue in a similar manner. Also, ends 34 and 36 would be respectively connected to tubings 50 and 48 of FIG. 7.

Attention is next directed to FIG. 6 where there is shown still another and probably preferred embodiment of the measurement catheter. Shown thereon is a double-lumened tube having channels 61 and 63 which connect respectively to annulus, bubble, or balloon 60. The end of the channels 61 and 63 of the double-lumened tube are sealed at 65. The communication between lumen 61 and lumen 63 is accomplished by means of hole 64 in lumen 61 and hole 66 in lumen 63. In flowing from hole 64 to hole 66, the fluid is contained within the thin-walled annulus, bubble, or balloon or chamber 60. Care must be exercised in sealing the tubes at location 65, so that the sealing process does not modify the compliance of the material of the bubble. Care must be exercised that the hole 64 is not too close to the end so that any change in compliance due to the sealing will not change the compliance of the bubble 60. The design, having the measurements shown, has worked satisfactorily, however, further engineering studies may develop even more efficient catheter design.

Our invention has many advantages. The invention allows for long term direct measurements, recording, and monitoring of tissue compartment pressures. All portions of the system which contact the patient can be sterilized. The fluid within the system is pre-sterilized to maintain sterility throughout the use of the invention. All portions of the system which contact the patients may be made as disposable units.

Further, this invention does not require the use of either intermittant or constant infusion of saline or other liquid into the patient's tissue. The chances, therefore, of increasing the tissue pressure and the result of increased possibility of tissue destruction by fluid injections are eliminated. This described system also eliminates any chance of backflow or obstruction of the catheter. Further, the measurement principal used by the described invention allowed the determination and monitoring of pressures, not only in tissue, but also in a variety of liquids or gels, even if they contain considerable solid particulate material. Muscle tissue is most comparable to a gel containing solid matter.

Various modifications can also be made to this invention. For example, unaltered sections, that is the part of the catheter that is not the thin-walled section, can be made out of stainless steel or other appropriate material. In still another embodiment, the measurement system can be arranged such that system flow is not maintained constant and the flow rate is used as the determinant of tissue pressure. This system can be made to function with flow, pressure, or a combination of both as variables used in the measurement of tissue pressure. Further, a variety of types of pumps including gear, vane, centrifugal, and peristaltic can be used for the system. Other transducer to measure system pressure and flow could be used with this invention.

While the invention has been described with particularity, it is manifest that many changes may be made in the details of construction and the arrangement of components without departing from the spirit and scope of the instant invention. It is understood that the invention is not limited to the embodiments set forth herein for purposes of exemplification, but is to be limited only by the scope of the attached claim or claims, including the full range of equivalency to which each element thereof is entitled.

What is claimed:

1. A catheter for use in measuring pressure in animal tissue which comprises a single long tubular member having only one lumen throughout and having a section having a wall more flexible than the rest: said long tubular member forms a U-shaped single flow channel open at each end and through which fluid may flow continuously, and said more flexible section is a part of said U-shaped flow channel and is near the bend of said U-shaped flow channel and is a bubble.

2. A catheter as defined in claim 1 in which said long tubular member has a non-perforated wall and such wall is impervious to animal tissue fluid.

* * * * *